United States Patent [19]

Garganese et al.

[11] Patent Number: 4,500,289

[45] Date of Patent: Feb. 19, 1985

[54] DENTURE OCCLUSAL MOUNTING TRANSLATOR

[76] Inventors: Ugo S. Garganese, 1790 Warwick Ave., Warwick, R.I. 02889; John R. Griffin, 5 Franconia St., Dorchester, Mass. 02122; Raymond H. Martin, 88 Brisbon Rd., Somerset, Mass. 02726

[21] Appl. No.: 405,427

[22] Filed: Aug. 5, 1982

[51] Int. Cl.³ .............................................. A61C 11/00
[52] U.S. Cl. ........................................... 433/54; 433/72
[58] Field of Search ........................ 433/55, 60, 54, 72

[56] References Cited

U.S. PATENT DOCUMENTS

| | | | |
|---|---|---|---|
| 2,376,384 | 5/1945 | Ringle et al. | 433/60 |
| 2,456,447 | 12/1948 | Ringle et al. | 433/60 |
| 2,567,810 | 9/1951 | Harper | 433/72 |
| 2,618,068 | 11/1952 | Apple | 433/72 |
| 2,959,857 | 11/1960 | Stoll | 433/55 |
| 3,206,852 | 9/1965 | Swanson | 433/73 |
| 4,337,039 | 6/1982 | Martin et al. | 433/60 |
| 4,391,589 | 7/1983 | Monfredo et al. | 433/55 |

*Primary Examiner*—Robert Peshock

[57] ABSTRACT

A denture occlusal mounting translator to transfer the patient's occlusal measurements in the exact location by the positioning of the model to set artificial teeth to the patient's interoral plane, eliminating the need of a wax occlusal rim.

1 Claim, 5 Drawing Figures

DENTURE OCCLUSAL MOUNTING TRANSLATOR

BACKGROUND OF THE INVENTION

The invention is directed to a new and novel attachment to a dental articulator and specifically for use in setting teeth to the patient's exact occlusal plane. It is also an object of this invention to eliminate the use of a so called wax occlusal rim universally used in dentistry which gives an arbitrary plane of occlusion and which is limited by the skill of the practitioner. The invention comprises a special occlusal mounting translator which is attached to the dental articulator and is adjustable to translate the measurements of the patients's incisal papilla to the upper lip at rest and the left and right hamular notch, which is the exact occlusal plane.

DESCRIPTION OF THE PREFERRED EMBODIMENTS

Figure 1:
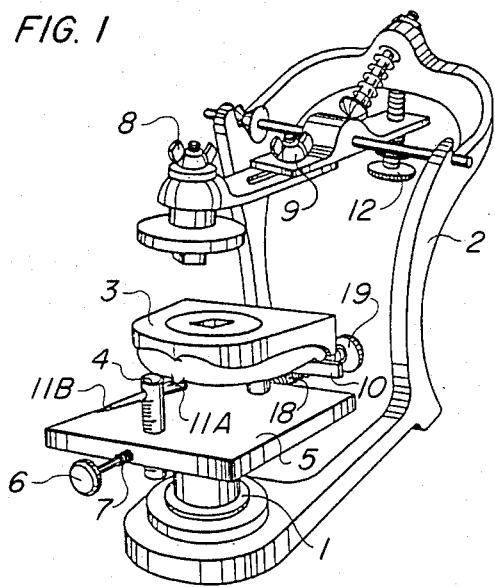
FIG. 1 shows occlusal translator mounted on a plasterless articulator with upper model or cast in position.

FIG. 1 shows occlusal mounting translator attached 1 to the base of the plasterless articulator 2 supporting the maxilliary cast 3. The patient's papilla to lip-line measurement is transfered to the occlusal mounting translator by setting the anterior vertical rod 4 to the exact elevation from the occlusal table 5 and locked into position using wrench 6 and set screw 7. The maxilliary cast is placed on the horizontal bar 10 at the hammular notches and elevated to leave space between the occlusal table 5 and the tuberosities of the maxilliary cast for denture base and locking in this position by set screw 19, The anterior papilla of the maxilliary cast is placed onto the pin 11a of the anterior vertical rod 4, and elevated to the measurement desired and locked by wrench 6 and set screw 7. The occulusal mounting translator is attached to the square holed base 1 to the lower member of the plasterless articulator 2, the two wing nuts 8 and 9 of the upper assembly of the articulator 2 are losened to allow free movement to engage the maxilliary cast 3 to the plasterless articulator and locked into position by tightening the wing nuts 8 and 9 and setting the vertical screw 12 of the articulator 2.

Figure 2:
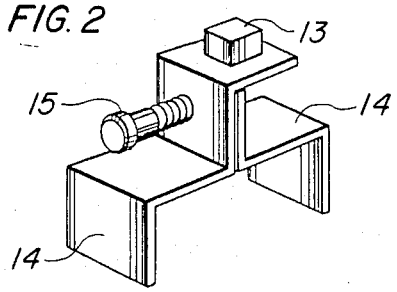
FIG. 2 shows adapter for mounting occlusal translator to other articulators.

FIG. 2 shows adapter with a square nut 13 for mounting the square holed base 1 of the occlusal mounting translator and adjustible clamp 14 to attach adapter to the base of other articulators by tightening screw 15.

Figure 3:
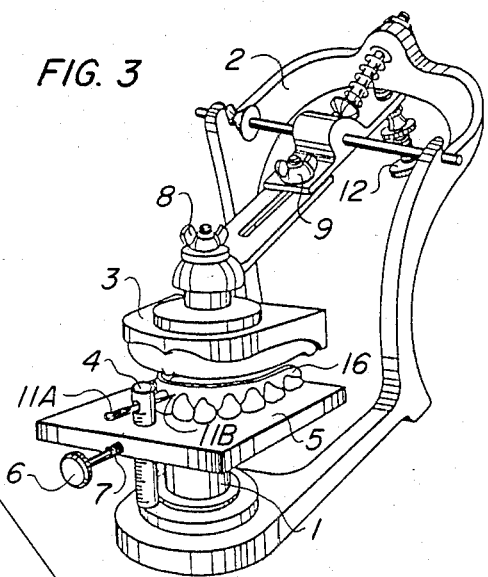
FIG. 3 shows occlusal translator mounted on a plasterless articulator with model in place and teeth placed on the occlusal table.

FIG. 3 shows teeth 16 placed on the occlusal table 5 and guided for positioning by pointer 11b of the anterior vertical rod 4 which is set by revolving rod 4 to bring pointer 11b to maxilliary cast papilla and bisecting the center of the maxilliary papilla and lowering it to the occlusal table 5 and locking to occlusal table 5 by wrench 6 and set screw 7.

Figure 4:
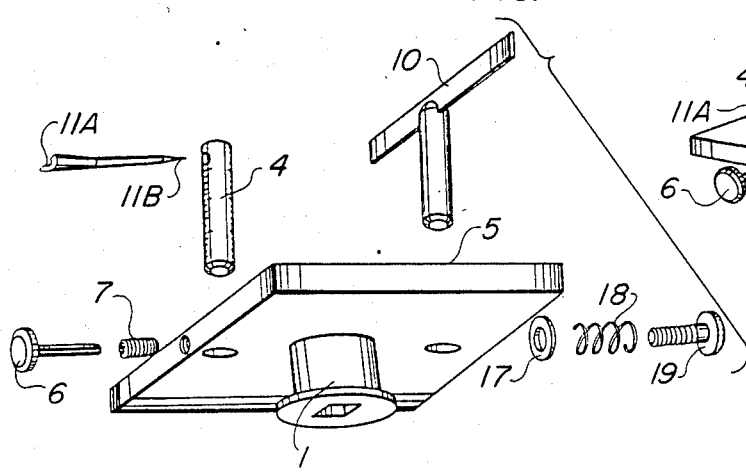
FIG. 4 shows an exploded view of the parts on the occlusal translator.

FIG. 4 shows exploded view of component parts with the square holed base 1 for attaching to the plasterless articulator 2 or adapter FIG. 2 at 13. Occlusal table 5 having a zero degree surface supporting the anterior vertical rod 4 which elevates for measuring distance from the zero degree table 5 and supporting pin 11a which cradles maxilliary cast papilla and pointer 11b for bisecting maxilliary cast papilla, and wrench 6 for locking anterior vertical rod 4. Zero degree table 5 also supporting horizontal bar 10 which allows revolving action and elevating movements and locking into position by wrench 19 and spring 18 and washer 17.

Figure 5B:
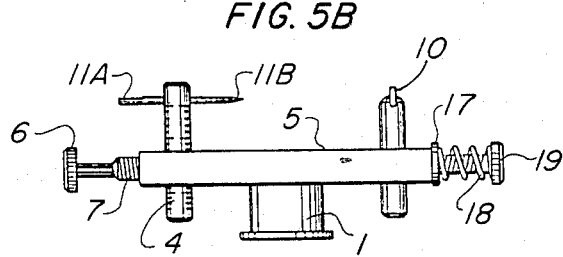
FIG. 5 shows occlusal translator, top, side, and bottom view.
Figure 5A:
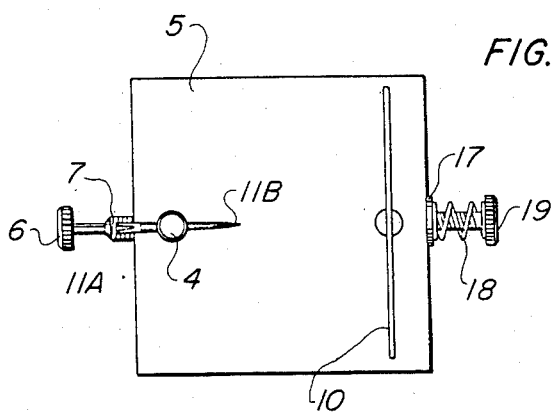

FIG. 5a showing top view of occlusal mounting translator looking onto occlusal table 5 anterior vertical rod 4 supporting pin 11a and pointer 11b, wrench 6 and set screw 7 to lock anterior vertical rod 4. Horizontal bar 10 and wrench 19 spring 18 and washer 17 for locking horizontal bar 10.

FIG. 5b showing side view of occlusal mounting translator attaching square holed base 1 to plasterless articulator 2 or adapter FIG. 2, 13. Occlusal table 5, anterior vertical rod 4 supporting pin 11a and pointer 11b wrench 6 and set screw 7 for locking anterior vertical rod 4 horizontal bar 10 wrench 19 spring 18 and washer 17 for locking the horizontal bar 10.

Figure 5C:
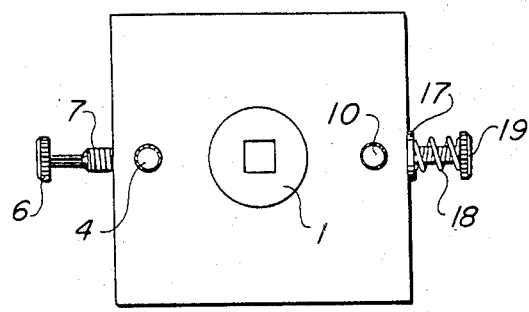

FIG. 5c showing the bottom view of occlusal mounting translator square holed base 1 for attaching to plasterless articulator 2 or adapter FIG. 2, 13 wrench 6 and set screw 7 for locking anterior vertical rod 4. Wrench 19 spring 18 and washer 17 for locking horizontal bar 10.

We claim:

1. A dental occlusal mounting translator for use with an articulator said translator is used to mount and set a dental cast of a patients maxilla to the patients exact occlusal plane in relation to the zero-degree table, said translator having a flat zero-degree table on which artificial teeth are to be set; said zero-degree table having an anterior elevating calibrated rod capable of swivel movements with a horizontal support pin grooved on one end for supporting the anterior papilla of the maxillary cast; a pointer on the opposite end of the pin for positioning of the arch of multiple artificial teeth said pointer located at the top section of the elevating calibrated rod; a posterior horizontal support bar for engaging the hammula notches of the maxilliary cast with elevating capabilities located at the opposite side of the zero-degree table from the calibrated papilla rod; a square holed mounting disc at the base of the zero-degree table and a mounting attachment for the translator table having adjustable clamp with a set screw for tightening to the base of articulator having mounting platform with a square protrusion at the top side to fit the square holed disc of the base of the translator table to secure the attachment and table together and a mounting attachment for insertion into the square holed disc for attaching the translator table to any articulator, said mounting attachment having adjustment clamp with a set screw for tightening to the base of any articulator.

* * * * *